US 7,960,332 B2

(12) United States Patent
Simonsen et al.

(10) Patent No.: US 7,960,332 B2
(45) Date of Patent: Jun. 14, 2011

(54) STABILIZATION OF GRANULES

(75) Inventors: Ole Simonsen, Soborg (DK); Erik Kjaer Markussen, Vaerlose (DK); Hanne Philbert Nielsen, Lyngby (DK); Lone Aslaug Hansen, Farum (DK)

(73) Assignee: Novozymes A/S, Bagsvaerd (DK)

( * ) Notice: Subject to any disclaimer, the term of this patent is extended or adjusted under 35 U.S.C. 154(b) by 287 days.

(21) Appl. No.: 10/543,081

(22) PCT Filed: Jan. 26, 2004

(86) PCT No.: PCT/DK2004/000050
§ 371 (c)(1),
(2), (4) Date: Jul. 22, 2005

(87) PCT Pub. No.: WO2004/067739
PCT Pub. Date: Aug. 12, 2004

(65) Prior Publication Data
US 2007/0032398 A1    Feb. 8, 2007

Related U.S. Application Data

(60) Provisional application No. 60/443,064, filed on Jan. 27, 2003.

(30) Foreign Application Priority Data

Jan. 27, 2003  (DK) ............................... 2003 00104

(51) Int. Cl.
C11D 3/386 (2006.01)
C11D 7/42 (2006.01)
C11D 17/06 (2006.01)

(52) U.S. Cl. ........ 510/441; 510/320; 510/349; 510/392; 510/477; 510/513; 510/530; 435/183; 435/184; 435/187

(58) Field of Classification Search ................. 510/441, 510/349, 320, 392, 513, 530, 477; 435/183, 435/184, 187
See application file for complete search history.

(56) References Cited

U.S. PATENT DOCUMENTS

| 3,630,930 | A | | 12/1971 | Davis et al. |
| 4,009,076 | A | * | 2/1977 | Green et al. ................. 435/187 |
| 4,016,041 | A | * | 4/1977 | van Kampen ................ 435/187 |
| 5,858,952 | A | | 1/1999 | Izawa et al. |
| 5,972,669 | A | | 10/1999 | Harz et al. |
| 6,242,407 | B1 | * | 6/2001 | Bertacchi et al. ............ 510/372 |
| 6,355,607 | B1 | * | 3/2002 | Rahman et al. .............. 510/446 |
| 6,423,517 | B2 | * | 7/2002 | Becker et al. ................ 435/187 |
| 6,602,843 | B2 | * | 8/2003 | Markussen .................. 510/392 |
| 2001/0044403 | A1 | * | 11/2001 | Markussen .................. 510/392 |

FOREIGN PATENT DOCUMENTS

| DE | 2020227 A * | 11/1971 |
| EP | 206417 | 12/1986 |
| GB | 1395330 | 5/1975 |
| GB | 1415301 | 11/1975 |
| GB | 2064543 | 6/1981 |
| JP | 61-168698 | 7/1986 |
| JP | 62-079298 | 4/1987 |
| JP | 03-149298 | 6/1991 |
| JP | 2001-157581 | 6/2001 |
| WO | WO 91/17235 | 11/1991 |
| WO | WO 99/32595 | 7/1999 |
| WO | WO 99/32612 | 7/1999 |
| WO | WO 00/01793 | 1/2000 |
| WO | WO 00/63336 | 10/2000 |
| WO | WO 01/40428 A1 * | 6/2001 |

* cited by examiner

*Primary Examiner* — Lorna M Douyon
(74) *Attorney, Agent, or Firm* — Michael W. Krenicky

(57) ABSTRACT

A coated granule including a core. The core includes a uniform mixture of a detergent enzyme having an alkaline pH activity optimum, and an acidic buffer component. The acidic buffer component has a pH of 1 to below 7 when measured as a 10% aqueous solution with a pKa in the range of 4 to 9.

24 Claims, No Drawings

STABILIZATION OF GRANULES

CROSS-REFERENCE TO RELATED APPLICATIONS

This application is a 35 U.S.C. 371 national application of PCT/DK2004/000050 filed Jan. 26, 2004, which claims priority or the benefit under 35 U.S.C. 119 of Danish application no. PA 2003 00104 filed Jan. 27, 2003 and U.S. provisional application No. 60/443,064 filed Jan. 27, 2003, the contents of which are fully incorporated herein by reference.

FIELD OF THE INVENTION

The present invention relates to granules comprising detergent enzymes and acidic buffer components in the core. The acidic buffer components serve the purpose of stabilising the detergent enzymes containing granules by neutralizing hostile alkaline materials in the environment. The invention further relates to processes of the manufacturer of said granules.

BACKGROUND OF THE INVENTION

It is known to the art to incorporate enzymes into dry solid particles or granules and thereby protect the enzymes from inactivation and/or protect the environment from the enzymes. It is further known to the art to incorporate stabilizers into such granule to protect the enzymes against inactivation caused by aggressive materials in the environment.

Known prior art related to stabilization of enzymes in dry granules are:
U.S. Pat. No. 5,858,952 discloses an enzyme-containing granulated product comprising an enzyme and one or more stabilizers selected from the group consisting of reducing agents and antioxidants. U.S. Pat. No. 5,972,669 discloses methods to improve the processing and storage stability of dry enzyme preparations. To this extend an inorganic salt, e.g. $MgSO_4$, is dissolved in an enzyme containing solution which is subsequently dried, using e.g. spray drying.

WO 91/17235 discloses granules containing enzymes and an enzyme protecting agent.

EP 206,417 discloses enzyme granular compositions comprising an enzyme core and alkaline buffer salt coating.

WO 00/01793 discloses coated enzyme granules wherein the coating comprises water soluble salt which may be slightly acidic.

GB 1,395,330 discloses use of amino acids in amylase granules.

GB 2,064,543 discloses granules containing an enzyme and sodium dihydrogen phosphate.

GB 1,415,301 discloses an enzyme granule comprising in the core alkali metal inorganic salts.

Measures to prevent the reduction of enzyme activity of enzyme-containing granulated products are disclosed by Japanese Patent Application Laid-Open (kokai) No. 62-79298, which describes an enzyme composition in which the core part containing an enzyme is coated with a protective layer containing an alkaline buffering salt of pH 7-11, and by Japanese Patent Application Laid-Open (kokai) No. 3-149298, which describes a bleaching agent containing hydrase particles, in which the enzyme nuclei are coated with a protective agent such as a water-soluble alkali metal silicate, a transition metal, or a reducing agent.

WO 99/32595 discloses enzyme granules comprising an enzyme core and a hydrated barrier material.

WO 99/32612 discloses granules comprising a protein mixed together with a salt, wherein the granules are prepared by fluid bed.

SUMMARY OF THE INVENTION

Reasons for formulating enzymes into particles, such as preparing enzyme granules include protection of the enzymes by separating it from the surrounding potentially hostile environment until the moment when the enzyme is to be used in an application.

The object of the present invention is to provide stabilized solid formulations of detergent enzymes, particularly formulations showing improved stability of the enzyme in hostile alkaline powder detergents.

Most detergent enzymes having an alkaline pH activity optimum are sensitive to alkaline compounds and get unstable in their presence, e.g. become unstable when getting into contact with alkaline components. The enzyme may also become unstable in the presence of other compounds which are hostile only due to the alkaline pH of powder detergents.

Hence the object of the invention is to improve solid formulations of detergent enzymes having an alkaline pH activity optimum with respect to stabilisation in alkaline environment. We have surprisingly found that this stability problem can be solved by means of controlling the pH in the environment closest to and surrounding the detergent enzyme having an alkaline pH activity optimum by adding acidic buffer components to the granules. Indeed it was surprising that detergent enzymes having an alkaline pH activity optimum could be stabilised by acidic compounds. Normally one would expect that an enzyme which functions optimally at alkaline pH would prefer and be more stabile in an alkaline environment of for example alkaline buffer salts.

Hence the present invention provides in a first aspect a coated granule comprising in the core a uniform mixture of a detergent enzyme having an alkaline pH activity optimum, and at least 10% w/w of acidic buffer component capable of neutralizing hostile alkaline compounds present in the environment, wherein said acidic buffer component has a pH of 1 to below 7 when measured as a 10% aqueous solution and a $pK_a$ in the range of 4 to 9.

The invention further provides methods for preparation of the granules and compositions comprising the granules.

BRIEF DESCRIPTION OF DRAWINGS

No figures.

DETAILED DESCRIPTION OF THE INVENTION

Introduction

The stability of detergent enzymes having an alkaline pH activity optimum, in granules, is influenced by the surrounding environment upon storage. Alkaline components have been found to deteriorate the stability of such detergent enzymes in granules.

The alkaline component might work directly as a destabilizer on the detergent enzyme or indirectly by having a positive effect on unwanted reactions such as oxidation processes.

By adding acidic buffer components to form a uniform mixture with the detergent enzyme in the core of coated the granules we have found that we are able of preventing the detergent enzyme in getting unstable in alkaline environments. The acidic buffer components work by neutralizing the hostile/unwanted alkaline components.

Some detergent enzymes get deactivated in too acidic environments. It is therefore important to investigate how acidic the environment can be before the detergent enzymes begin to deactivate and therefore it is important to adjust the pH in the granule accordingly. We have found that a way to solve the above mentioned problem, is by either adding less acidic buffer components to the core comprising the detergent enzyme or adding acidic buffer components with a not too low pH in solution to the core comprising the detergent enzyme thereby being able of regulating pH in the granule in a way not stressing the detergent enzyme.

Optionally the coating of the granule of the invention may also contain an acidic buffer of the invention. However, in a particular embodiment of the present invention more than 20% w/w of the total amount of acidic buffer component present in the granule is present in the core, more particularly more than 40% w/w of the total amount, more particularly more than 60% w/w of the total amount, more particularly more that 70% w/w of the total amount, more particularly more that 80% w/w of the total amount, more particularly more that 90% w/w of the total amount, more particularly more that 95% w/w of the total amount of acidic buffer component is present in the core.

In a particular embodiment of the present invention the acidic buffer component in the core has a pH of 4 to below 7 and the optional acidic buffer component in the coating has a pH of 1 to 5.

In a further particular embodiment of the present invention the pH of the acidic buffer component used in the core is 4.5 to below 7, in another particular embodiment of the present invention the pH of the optional acidic buffer component used in the coating is less than 4.5. An example is to use sodium hexametaphosphate (with a pH in a 10% solution of around 6.5) or disodiumhydrogencitrate (with a pH in a 10% solution of around 4.8) in the core and optionally $NaH_2PO_4$ or $KH_2PO_4$ (with a pH in 10% solution of around 4.2) in the coating. The acidic buffer component used in the core may even be chosen so as the provide buffer capacity towards the optional acidic buffer in the coating.

By adding acidic buffer components both to the core and the coating the buffer capacity of the granule is increased. In a further particular embodiment of the present invention the acidic buffer component in the core and the optional acidic buffer in the coating is the same.

We have further found that acidic buffer components work very well as regulating agents for solubility of the granules. An important feature of many granules comprising detergent enzymes having an alkaline pH activity optimum is their solubility and release time of the detergent enzymes i.e. increasing or decreasing the release time of the detergent enzymes in to aqueous solutions. In many applications it is important that the detergent enzymes are released at a specific desired point in time. By using acidic buffer components with different solubility properties in the core and optionally in the coating it is possible to regulate and control the release time of the detergent enzymes to a given environment, e.g. making a delayed release or a slow release or a combination thereof.

Hence, in a particular embodiment of the present invention the acidic buffer component used in the core is less soluble or having a slower solubility rate in aqueous environment, compared to the components including any optional acidic buffer component used in the coating, typically giving as low release of the detergent enzymes (compared to using the more soluble or faster soluble acidic buffer both in the core and in the coating). An example is to use $Ca(H_2PO_4)_2$ which has a solubility of less than 2% in water at 10° C. in the core and optionally $NaH_2PO_4$ which has a solubility around 40% at 10° C. in the coating.

In another particular embodiment of the present invention the acidic buffer component used in the core is more soluble or having a faster solubility rate in aqueous environment, compared to the components including any optional acidic buffer component used in the coating, typically giving a delayed release of the detergent enzymes (compared to using the more soluble or faster soluble acidic buffer both in the core and in the coating). An example is to use $Ca(H_2PO_4)_2$ which has a solubility of less than 2% in water at 10° C. in the coating and $NaH_2PO_4$ which has a solubility around 40% at 10° C. in the core.

In another particular embodiment of the present invention the acidic buffer component used in the core is more soluble or having a faster solubility rate in aqueous environment, typically giving a rapid release of the detergent enzymes. An example is to use $NaH_2PO_4$ which has a solubility around 40% at 10° C. in the core.

Solubility properties can also be changed by using polyacrylic acid copolymers where the solubility and solubility rate can be varied almost arbitrarily by the use of different monomers (e.g. hydrophilic or hydrophobic) and varying the ratio between the used monomers.

Acidic Buffer Component

In the context of the present invention the term "acidic buffer component" is to be understood as a component which is at least partly on its acid form, which can neutralize alkaline compounds and thus comprise a buffer capacity towards an increase in pH. With alkaline compounds in the present invention is understood components which has a pH higher than 8 in a 10% w/w aqueous solution. The acidic buffer component of the present invention may be any acidic buffer component or mixture of acidic buffer components, accordingly, when reference is made to "acidic buffer component" this will in general be understood to include combinations of one or more acidic buffer components.

The suitable acidic buffer component of the present invention has a pH of less than 7 when measured in a 10% aqueous solution. In a particular embodiment of the present invention the acidic buffer component has a pH of 1 to below 7, in a more particular embodiment the acidic buffer component has a pH of 3 to below 7, in a most particular embodiment the acidic buffer component has a pH of 4 to 5.

Furthermore the acidic buffer component of the present invention has a $pK_a$ from 2 to 9, in particular a $pK_a$ from 4 to 9, in particular a $pK_a$ from 5 to 8, in particular a $pK_a$ from 2 to 6, in particular a $pK_a$ from 2 to 5, in particular a $pK_a$ from 2 to 4, in particular a $pK_a$ from 5 to 7. To utilize most of the potential buffer capacity the pH of an aqueous solution is in general below the $pK_a$ $pK_a$ is defined as $$pK_a = -\log K_a$$

wherein $K_a$ is the acidity constant. See T. W. Graham Solomons, Fundamentals of Organic Chemistry, fourth edition, p. 92 to p. 94, (ISBN 0-471-30562-6).

The pH of the acidic buffer component is measured as 10% w/w aqueous solution of the acidic buffer component.

To obtain the best protection of the detergent enzyme it is important that the granule core, and optionally the coating comprise enough buffer capacity to withstand the hostile alkaline components in the environment. It is found that the granule core must comprise at least 10% w/w of acidic buffer component, in particular more than 25% w/w of acidic buffer component, in particular more than 40% w/w of acidic buffer component, in particular more than 50% w/w of acidic buffer component, in particular more than 60% w/w of acidic buffer component, in particular more than 70% w/w of acidic buffer component, in particular more than 80% w/w of acidic buffer component. If the coating includes an acidic buffer component it should particularly constitute more than 40% w/w of the coating, more particularly more than 50% w/w of the coating.

Particularly, suitable acidic buffer components of the present invention are salts of $H_3PO_4$ e.g. $NaH_2PO_4$, $KH_2PO_4$, and $Ca(H_2PO_4)_2$, polyphosphates e.g. sodium hexametaphosphate, polyacrylic acid and partly neutralized polyacrylic acid and co-polymers thereof, simple organic acids (less than 10 carbon atoms e.g. 6 or less carbon atoms) such as citric acid and salts thereof such as hydrogen citrate, e.g. disodium hydrogen citrate, malonic, succinic, glutaric, adipic acid.

In a particular embodiment of the present invention the acidic buffer components are selected from the group consisting of polyacrylic acid and partly neutralized polyacrylic acid and co-polymers thereof, citric acid and $Na_2H$-citrate.

In an even more particular embodiment of the present invention the acidic buffer components are selected from the group consisting of phosphates such as $NaH_2PO_4$, $KH_2PO_4$, $Ca(H_2PO_4)_2$ and sodium hexametaphosphate or mixtures thereof.

The acidic buffer component(s) is present in the core and optionally in the coating. In a particular embodiment of the present invention there is only acidic buffer component in the core, in a more particular embodiment of the present invention the acidic buffer component is only present in the coating, in a most particular embodiment the acidic buffer component is both present in the core and in the coating. In a further embodiment of the present invention the acidic buffer component in the core and in the coating are different.

The Core

The core unit comprises a detergent enzyme having an alkaline pH activity optimum and the acidic buffer component. In a particular embodiment of the present invention the core comprise acidic buffer component. In a particular embodiment of the present invention the core comprises at least 25% w/w of acidic buffer component, in a more particular embodiment the core comprises at least 40% w/w of acidic buffer component, in an even more particular embodiment the core comprises at least 60% w/w of acidic buffer component. In a further particular embodiment of the present invention the core comprises 50 to 95% w/w of acidic buffer component; in a most particular embodiment of the present invention the core comprises 60 to 90% w/w of acidic buffer component.

The acidic buffer component in the core has in a particular embodiment of the present invention at least a pH of 2 when measured as a 10% w/w aqueous solution. In a more particular embodiment of the present invention the acidic buffer component in the core has a pH of at least 4 when measured as a 10% w/w aqueous solution. In an even more particular embodiment the acidic buffer component has a pH of 3 to below 7. In a most particular embodiment the acidic buffer component has a pH of 4 to 6.

Furthermore the acidic buffer component in the core has a $pK_a$ of 4 to 9. In a particular embodiment of the present invention the $pK_a$ is 5 to 8, in a more particular embodiment the $pK_a$ of the acidic buffer component in the core is 5 to 7. To utilize most of the potential buffer capacity the pH of an aqueous solution is in general below the $pK_a$.

Besides of the detergent enzyme and the acidic buffer component, mentioned vide supra, the core may be constructed in any way or of any material which provides the desired functional properties of the core, e.g. the core may consist of materials which allow readily release of the detergent enzyme upon introduction to an aqueous medium.

Any conventional methods and non-active materials may be used to prepare the core. Examples of known conventional cores and materials are, inter alia, described in, U.S. Pat. No. 4,106,991 (in particular), EP 170360, EP 304332, EP 304331, EP 458849, EP 458845, WO 01/25412, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492, PCT/DK01/00627.

The core may besides the detergent enzymes having an alkaline pH activity optimum and acidic buffer component comprise fillers, binders, fiber materials, liquid agents, detergent enzyme stabilizing agents or detergent enzyme protective agents e.g. antioxidants, cross linking agents, plastizisers, inorganics, dispersing agents, viscosity regulating agents and solubilising agents.

Detergent Enzymes Having an Alkaline pH Activity Optimum

The detergent enzymes having an alkaline pH activity optimum of the present invention may be any detergent enzyme or mixture of detergent enzymes, which benefits from being separated from the environment surrounding the particle/granule.

The detergent enzyme in the context of the present invention may be any enzyme or combination of different enzymes useful as a detergent additive. Accordingly, when reference is made to "an enzyme" this will in general be understood to include combinations of one or more enzymes.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk), EP 525,610 (Solvay) and WO 94/02618 (Gist-Brocades NV).

The enzyme classification employed in the present specification with claims is in accordance with *Recommendations (1992) of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)]. An Example of a commercially available oxidoreductase (EC 1.-.-.-) is Gluzyme™ (enzyme available from Novozymes A/S). Further oxidoreductases are available from other suppliers. Preferred transferases are transferases in any of the following sub-classes:

a) Transferases transferring one-carbon groups (EC 2.1);
b) transferases transferring aldehyde or ketone residues (EC 2.2); acyltransferases (EC 2.3);
c) glycosyltransferases (EC 2.4);
d) transferases transferring alkyl or aryl groups, other that methyl groups (EC 2.5); and
e) transferases transferring nitrogeneous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches or cellulose) of especially five- and six-membered ring structures (i.e. glycosidases, EC 3.2), but also enzymes capable of isomerzing carbohydrates, e.g. six-membered ring structures such as D-glucose to five-membered ring structures such as D-fructose.

Carbohydrases of relevance include the following (EC numbers in parentheses): α-amylases (EC 3.2.1.1), β-amylases (EC 3.2.1.2), glucan 1,4-α-glucosidases (EC 3.2.1.3), endo-1,4-beta-glucanase (cellulases, EC 3.2.1.4), endo-1,3 (4)-β-glucanases (EC 3.2.1.6), endo-1,4-β-xylanases (EC 3.2.1.8), dextranases (EC 3.2.1.11), chitinases (EC 3.2.1.14), polygalacturonases (EC 3.2.1.15), lysozymes (EC 3.2.1.17), β-glucosidases (EC 3.2.1.21), α-galactosidases (EC 3.2.1.22), β-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-lucosidases (EC3.2.1.41), sucrose α-glucosidases (EC 3.2.1.48), glucan endo-1,3-α-glucosidases (EC 3.2.1.59), glucan 1,4-β-glucosidases (EC 3.2.1.74), glucan endo-1,6-β-glucosidases (EC 3.2.1.75), arabinan endo-1,5-α-L-arabinosidases (EC 3.2.1.99), lactases (EC 3.2.1.108), chitosanases (EC 3.2.1.132) and xylose isomerases (EC 5.3.1.5).

Examples of commercially available proteases (peptidases) include Kannase™, Everlase™, Esperase™, Alcalase™, Neutrase™, Durazym™, Savinase™, Pyrase™, Pancreatic Trypsin NOVO (PTN), Bio-Feed™ Pro and ClearLens™ Pro (all available from Novozymes A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipoprime™ Lipolase™, Lipolase™ Ultra, Lipozyme™, Palatase™, Novozym™ 435 and Lecitase™ (all available from Novozymes A/S).

Other commercially available lipases include Lumafast™ (*Pseudomonas mendocina* lipase from Genencor International Inc.); Lipomax™ (*Ps. pseudoalcaligenes* lipase from Gist-Brocades/Genencor Int. Inc.; and *Bacillus* sp. lipase from Solvay enzymes). Further lipases are available from other suppliers.

Examples of commercially available carbohydrases include Alpha-Gal™, Bio-Feed™ Alpha, BioFeed™ Beta, Bio-Feed™ Plus, Bio-Feed™ Plus, Novozyme™ 188, Celluclast™, Cellusoft™, Ceremyl™, Citrozym™, Denimax™, Dezyme™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™, (Amyloglucosidase Novo), Maltogenase™, Sweetzyme™ and Aquazyme™ (all available from Novozymes A/S). Further carbohydrases are available from other suppliers.

Fillers

Suitable fillers are water soluble and/or insoluble inorganic salts such as finely ground alkali sulphate, alkali carbonate and/or alkali chloride), clays such as kaolin (e.g. Speswhite™, English China Clay), bentonites, talcs, zeolites, chalk, calcium carbonate and/or silicates.

Binders

Suitable binders are binders with a high melting point or no melting point at all and of a non waxy nature e.g. polyvinyl pyrrolidon, dextrins, polyvinylalkohol, cellulose derivatives, for example hydroxypropyl cellulose, methyl cellulose or CMC. A suitable binder is a carbohydrate binder such as Glucidex 21D available from Roquette Freres, France.

Fiber Materials

Pure or impure cellulose in fibrous form such as sawdust, pure fibrous cellulose, cotton, or other forms of pure or impure fibrous cellulose. Also, filter aids based on fibrous cellulose can be used. Several brands of cellulose in fibrous form are on the market, e.g. CEPO and ARBOCELL. In a publication from Svenska Trämjolsfabrikema AB, "Cepo Cellulose Powder" it is stated that for Cepo S/20 cellulose the approximate maximum fiber length is 500 µm, the approximate average fibre length is 160 µm, the approximate maximum fibre width is 50 µm and the approximate average fibre width is 30 µm. Also, it is stated that CEPO SS/200 cellulose has an approximate maximum fibre length of 150 µm, an approximate average fibre length of 50 µm, an approximate maximum fiber width of 45 µm and an approximate average fiber width of 25 µm. Cellulose fibers with these dimensions are very well suited for the purpose of the invention. The words "Cepo" and "Arbocel" are Trade marks. A preferred fibrous cellulose is Arbocel™ BFC200. Also synthetic fibres may be used as described in EP 304331 B1 and typical fibres may be made of polyethylene, polypropylene, polyester, especially nylon, polyvinylformat, poly(meth)acrylic compounds.

Liquid Agents

A liquid agent is used in conventional mixer granulation processes for enabling the build up or agglomeration of the conventional granulating component particles into granules. The liquid agent is water and/or a waxy substance. The liquid agent is always used in a liquid phase in the granulation process but may later on solidify; the waxy substance if present, therefore, is either dissolved or dispersed in the water or melted. By the term "waxy substance" as used herein is meant a substance which possesses all of the following characteristics 1) the melting point is between 30 and 100° C., preferably between 40 and 60° C., 2) the substance is of a tough and not brittle nature, and 3) the substance possesses a certain plasticity at room temperature. Both water and waxy substance are liquid agents, i.e. they are both active during the formation of the granules; the waxy substance stays as a constituent in the finished granules, whereas the majority of the water is removed during a drying step.

Examples of waxy substances are polyglycols, fatty alcohols, ethoxylated fatty alcohols, mono-, di- and triglycerolesters of higher fatty, acids, e.g. glycerol monostearate, alkylarylethoxylates, and coconut monoethanolamide.

Enzyme Stabilizing or Enzyme Protecting Agents

Enzyme stabilizing or protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, -carbonates or bicarbonates which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate. Also enzyme stabilizers may be borates, borax, formates, di- and tricarboxylic acids and so called reversible enzyme inhibitors such as organic compounds with sulfhydryl groups or alkylated or arylated boric acids.

Cross Linking Agents

Cross linking agents may be enzyme compatible surfactants e.g. ethoxylated alcohols, especially ones with 10 to 80 ethoxy groups.

Further suspension agents, mediators (for boosting bleach action upon dissolution of the granule in e.g. a washing application) and/or solvents may be incorporated in the granule core.

In a particular embodiment of the present invention the core is the so called T-granulate wherein detergent enzymes and granulation material are mixed to form granules incorporating the detergent enzyme distributed throughout the core such as described in U.S. Pat. No. 4,106,991 e.g. example 1.

In one particular embodiment the core unit is constructed of a particulate carrier (I) with the detergent enzyme absorbed, and/or an detergent enzyme containing layer (II) applied, on the carrier surface, optionally comprising a protecting reducing agent. There may even be additional coating within the core unit material providing desired functional properties of the core unit material.

The core unit may be in any physical state, such as solid, liquid or gel. In a particular embodiment the core unit is in a solid state.

As a particular embodiment of the invention the core unit may be prepared by applying a detergent enzyme containing layer onto a "placebo" carrier (enzyme free carrier) coated with a layer containing the detergent enzyme according to the methodology described in e.g. WO 97/39116 or EP 0 193 829. Optionally additional detergent enzymes may be absorbed into the surface of the carrier.

In one embodiment of the invention the core unit may be as the core unit described in WO 01/25412. Such core unit may, in terms of its relative mass, comprise up to about 30% W/w, such as up to about 20% w/w, in particular up to about 15% w/w, more particularly up to about 10% w/w, such as up to about 5% w/w of the overall mass of the finished granule.

The Coating

The granule is further coated with one or more coating layers to provide additional properties of the granule.

The coating of the present invention may comprise acidic buffer component such as mentioned vide supra. In a particular embodiment of the present invention the coating comprises at least 10% w/w of acidic buffer component, in a more particular embodiment the coating comprises at least 30% w/w of acidic buffer component, in an even more particular embodiment the coating comprises at least 50% w/w of acidic buffer component. In a most particular embodiment the coating comprises at least 70% w/w of acidic buffer component, in a further particular embodiment of the present invention the coating comprises 10 to 100% w/w of acidic buffer component; in a more particular embodiment of the present invention the coating comprises 30 to 95% w/w of acidic buffer component, in a most particular embodiment of the present invention the coating comprises 60 to 90% w/w of acidic buffer component.

The acidic buffer component in the coating has in particular the pH and/or $PK_a$ mentioned supra.

For lowering formation of dust, the coating is preferably substantially free of detergent enzymes.

The coating may perform any of a number of functions in the granule, depending on the intended use of the granule. Thus, for example, an additional coating may achieve one or more of the following effects:
(i) further reduction of the dust-formation tendency of a granule without the additional coating according to the invention;
(ii) further protection of the active compound in the granule against hostile compounds e.g. oxidation by bleaching substances/systems (e.g. perborates, percarbonates, organic peracids and the like);
(iii) dissolution at a desired rate upon introduction of the granule into a liquid medium (such as an aqueous medium);
(iv) provide a better physical strength of the granule.

Conventional coatings and methods as known to the art may suitably be used, such as the coatings described in U.S. Pat. No. 4,106,991, EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492.

Besides acidic buffer components the coating may comprise materials selected from binders, fibers, salts, water insoluble minerals, pigments, dyes, enzyme stabilizers or combinations thereof and any granulation materials mentioned vide supra in the section "The core".

The coating may further comprise one or more of the following: antioxidants, reducing agents, chlorine scavengers, plasticizers, pigments, lubricants (such as surfactants or antistatic agents) and fragrances.

Examples of suitable antioxidants and reducing agents of the present invention are salts of alkali metals and earth alkali metals, salts of sulfite, thiosulfite, thiosulfate, erythorbate, citrate, isopropyl citrate and ascorbate or corresponding acids, silicates, carbonates or bicarbonates, phosphates and nitrit, other suitable materials are methionine, glycine, propyl gallate, tert-butyl hydroquinone, tocopherols, thiodipropionic acid, butylated hydroxytoluene (BHT), butylated hydroxyanisol (BHA) or tannic acid. In particular salts of thiosulfates, e.g. sodium thiosulfate, are suitable.

Plasticizers useful in the coating in the context of the present invention include, for example: polyols such as sugars, sugar alcohols, or polyethylene glycols (PEGs) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As an additional coating layer a lubricant may be applied to the granule. In a particular embodiment the granule comprise an enzyme containing core, a coating and an additional lubricant coating.

As used in the present context, the term "lubricant" refers to any agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents.

Examples of suitable lubricants are polyethylene glycols (PEGs) and ethoxylated fatty alcohols.

In appropriate embodiments of granules according to the present invention, the coating layer may be composed as described in U.S. Pat. No. 4,106,991, e.g. with a waxy material such as polyethylene glycol (PEG), optionally followed by powdering with a whitener such as titanium dioxide.

Preparation of the Granules

The invention also relates to a method for the preparation of the detergent enzyme containing granule described herein.

In a particular embodiment of the present invention the invention includes a process for preparing coated granules of the invention comprising preparing a core comprising a detergent enzyme having an alkaline pH activity optimum and at least 10% w/w of acidic buffer component having a pH of 1 to below 7 when measured as a 10% aqueous solution and a $pK_a$ in the range of 4 to 9, capable of neutralizing hostile alkaline compounds present in the environment, and coating the core with a coating material.

Preparation of the Core

Methods for preparing the core particles include known enzyme granule formulation technologies e.g. spray drying, fluid bed, fluidized spray drying, spray fluidizing, mixer granulation and extrusion. Other relevant core particles are layered products, absorbed products, pelletized products, prilled products. The cores may optionally be dried after granulation.

Spray dried products, wherein a liquid solution comprising detergent enzymes is atomised in a spray drying tower to form small droplets which during their way down the drying tower dry to form an detergent enzyme-containing particulate material. Very small particles can be produced this way (Michael S. Showell (editor); Powdered detergents; Surfactant Science Series; 1998; vol. 71; page 140-142; Marcel Dekker).

Layered products, wherein the detergent enzyme is coated as a layer around a preformed inert core particle, wherein an detergent enzyme-containing solution is atomised, typically in a fluid bed apparatus wherein the pre-formed core particles are fluidised, and the detergent enzyme-containing solution adheres to the core particles and dries up to leave a layer of dry detergent enzyme on the surface of the core particle. Particles of a desired size can be obtained this way if a useful core particle of the desired size can be found. This type of product is described in e.g. WO 97/23606.

In a particular embodiment of the present invention the synthetic polymer and/or the poly-saccharide and/or the protein source and or the antioxidants are mixed together with a liquid e.g. enzyme concentrate or fermentation broth and then atomised onto preformed cores in a coating chamber e.g. a fluid bedf, a multistage fluid bed, a fluid bed spray drier optionally with recirculation of fine particles.

Absorbed core particles, wherein rather than coating the detergent enzyme as a layer around the core, the enzyme is absorbed onto and/or into the surface of the core. Such a process is described in WO 97/39116.

Extrusion or pelletized products, wherein an detergent enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the detergent enzyme containing paste, which is harmful to the detergent enzyme. (Michael S. Showell (editor); Powdered detergents; Surfactant Science Series; 1998; vol. 71; page 140-142; Marcel Dekker). In a particular embodiment of the present invention the synthetic polymer and/or the polysaccharide and/or the protein source and/or the antioxidants are mixed together with a liquid e.g. enzyme concentrate or fermentation broth and then extruded.

Prilled products, wherein an detergent enzyme powder is suspended in molten wax and the suspension is sprayed, e.g. through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. No. 4,016,040 and U.S. Pat. No. 4,713,245 are documents relating to this technique Mixer granulation products, wherein a detergent enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the detergent enzyme. Such a process where the detergent enzyme is enzyme is described in U.S. Pat. No. 4,106,991 (NOVO NORDISK) and related documents EP 170360 B1 (NOVO NORDISK), EP 304332 B1 (NOVO NORDISK), EP 304331 (NOVO NORM ISK), WO 90/09440 (NOVO NORDISK) and WO 90/09428 (NOVO NORDISK). In a particular product of this process wherein various high-shear mixers can be used as granulators, granulates consisting of the enzyme, fillers and binders etc. are mixed with cellulose fibres to reinforce the particles to give the so-called T-granulate. Reinforced particles, being more robust, release less enzymatic dust.

Methods for preparing a viscoelastic liquid core particle include those described in WO 02/28991 and is hereby incorporated by reference.

In a further particular embodiment of the present invention the cores are prepared by a method comprising:
a) Preparing a particulate carrier material,
b) introducing a liquid medium comprising an detergent enzyme by atomization of the liquid medium into the fluid bed, so as to deposit nonvolatile components including the detergent enzyme of the liquid medium as an detergent enzyme containing layer on the carrier, and
c) removing volatile components of the liquid medium from the cores.

The particulate carrier material may in a preferred embodiment comprise a binder (such as Glucidex™ 21D, from Roquette Freres), a fibre material (such as cellulose fibres) and a filler (such as finely ground sodium sulfate and/or kaolin). The particulate carrier may as well be prepared/granulated and dried as described in Example 1 in U.S. Pat. No. 4,106,991. Following granulation the dry particulate carrier may suitably be sieved, and fractionated after size to obtain a uniform carrier size. In a preferred embodiment the carrier material comprises sugar and/or starch cores, nonpareils and inorganic salt particles or crystals e.g. $Na_2SO_4$ particles. Preferred carrier sizes measured as the diameter of the carrier are between 0.1-2 mm, e.g. 0.3-1.0 mm.

As a further particular embodiment additional detergent enzyme may be absorbed on the particulate carrier prior to applying the detergent enzyme layer (II), this absorption may be achieved by:
a) absorbing the component(s) into the surface of the carrier by contacting the particulate carrier with a liquid comprising the detergent enzyme in a mixer,
b) mixing the composition by means of mixing blades, and c) drying the detergent enzyme loaded carrier by fluidising it in a fluid bed apparatus.

Conventional mixing equipment can satisfactorily be used to mix the particulate carrier with the detergent enzyme-containing liquid medium. The mixing equipment can be a batch mixer or a continuous mixer, such as a convective mixer, see, e.g. Hamby et al., Mixing in the Process Industries, pp. 39-53 (ISBN 0-40811574-2). Non-convective mixing equipment, e.g. rotating drum mixers or so-called pan-granulators, may also be employed.

Drying of detergent enzyme-loaded particulate carrier, application of the detergent enzyme containing layer (II) the coating (III) and any additional coatings may be performed in any type of fluidising equipment (such as in a fluid-bed apparatus or other form of fluidizing equipment, such as a Hüttlin-type fluidizer). For a description of suitable fluid-bed equipment, see, e.g., Hamby et al., Mixing in the Process Industries, pp. 54-77 (ISBN 0-408-11574-2).

Preparation of the Coating

Conventional coatings and methods as known to the art may suitably be used, such as the coatings described in Danish PA 2002 00885, Danish PA 2002 00473, WO 89/08694, WO 89/08695, 270 608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, WO 01/25412, WO 02/20746, WO 02/28369, U.S. Pat. No. 5,879,920, U.S. Pat. No. 5,324,649, U.S. Pat. No. 4,689,297, U.S. Pat. No. 6,348,442, EP 206417, EP 193829, DE 4344215, DE 4322229 A, DE 263790, JP 61162185 A and/or JP 58179492.

The coating may be prepared by the same methods as mentioned vide supra in the section "Preparation of the core".

Methods for production of the detergent enzyme containing granule of the present invention may comprise the following steps:
a) mixing detergent enzyme and acidic buffer component containing cores with a liquid coating medium comprising a water soluble compound and,
b) removing volatile components of the liquid medium from the mixture, so as to deposit the nonvolatile components of the liquid coating medium as solid coating layer on the cores, or
a) mixing detergent enzyme containing cores with a liquid coating medium comprising the acidic buffer component and,
b) removing volatile components of the liquid coating medium from the mixture, so as to deposit the nonvolatile components of the liquid coating medium as solid coating layer on the cores, or
a) mixing detergent enzyme and acidic buffer component containing cores with a liquid coating medium comprising the acidic buffer component and,
b) removing volatile components of the liquid medium from the mixture, so as to deposit the nonvolatile components of the liquid coating medium as solid coating layer on the cores, or
a) mixing detergent enzyme and acidic buffer component containing cores with a melted coating medium and,
b) cooling to obtain a solid coating layer on the cores, or
a) mixing detergent enzyme and acidic buffer component containing cores with a melted coating medium comprising the acidic buffer component and,
b) cooling to obtain a solid coating layer on the cores.

In a particular embodiment of the present invention the detergent enzyme containing granule is produced by a fluid bed process comprising:
a) fluidising an detergent enzyme and acid buffer containing core material in a fluid bed apparatus,
b) introducing a liquid medium comprising a water soluble compound by atomization of the liquid coating medium into the fluid bed, so as to deposit non-volatile components of the liquid medium as a solid coating layer on the core material and,
c) removing volatile components of the liquid medium from the coated core material.

Compositions Comprising the Coated Particle and their Application

The invention also relates to compositions comprising the granules of the invention. The composition may be any composition, but particularly the compositions are well suited for use in the detergent industry, in the textile industry, in the feed industry and in the baking industry. Accordingly the compositions may be detergent compositions, a feed composition, a baking composition or an additive to be incorporated in such compositions.

Detergents

The coated particles of the invention may be added to and thus become a component of a detergent composition comprising alkaline components.

The detergent composition of the invention may for example be formulated as laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

In a specific aspect, the invention provides a detergent additive comprising the coated particles of the invention. The detergent additive as well as the detergent composition may comprise one or more enzymes than that in the granules of the invention such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases Include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include EVERLASE™, OVOZYME™, SAVOZYME™, ALCALASE™, SAVINASE™, PRIMASE™, DURALASE™, ESPERASE™, AND KANNASE™ (Novozymes A/S), MAXATASE™, MAXACAL™, MAXAPEM™, PROPERASE™, PURAFECT™, PURAFECT OXP™, FN2™, and FN3™, FN4™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™, PURASTAR™ and PURASTAR OXAM™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarum, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,767 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include GUARDZYME™ (Novozymes A/S).

Mannanase: Suitable mannanases include MANNAWAY™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, may be formulated so as to contain one or more of the particles of the invention comprising different enzymes.

The detergent composition of the invention may be in any convenient dry form, e.g., a bar, a tablet, a powder, a granule or a paste. It may also be a liquid detergent, in particular nonaqueous liquid detergent.

The detergent composition comprises one or more surfactants, which may be nor-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system, which may comprise a H2O2 source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, may be added in an amount corresponding to 0.01-100 mg of enzyme protein per liter of wash liquor, preferably 0.055 mg of enzyme protein per litre of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

EXAMPLES

Example 1

Uncoated protease granulates were produced as described in U.S. Pat. No. 4,106,991 example 1 with the following exceptions:

- A small scale high shear mixer (Mi-Mi-Pro granulator from Pro-C-epT) was used in stead of a Lödige mixer
- Finely grinded sodium sulfate was used in stead of sodium chloride as filler material
- Finely grinded buffer salt was added according to the table below
- The enzyme concentrate (added as a liquid) contained also a carbohydrate binder (Avedex W80 dextrin)

The storage stability of the produced granulates in an ADW powder A (stored 7 days at 40° C. and 60% RH) was tested:

| Buffersalt | % residual activity |
| --- | --- |
| None (reference) | 40 |
| 25% NaH$_2$PO$_4$ | 53 |
| 60% NaH$_2$PO$_4$ | 78 |
| 25% KH$_2$PO$_4$ | 61 |
| 60% KH$_2$PO$_4$ | 84 |
| 25% Na$_2$H-citrate | 61 |
| 60% Na$_2$H-citrate | 65 |

Addition of buffer salt increases stability. The best results are obtained with a high content of buffer (>25%) and the phosphates are more efficient than citrate.

Example 2

Uncoated Savinase granulates were produced as in example 1 with Na$_2$SO$_4$ as filler material and using a Lödige mixer. The uncoated granules were coated in a fluid bed (Hüttlin Kugel-Coater) with 2% sodium thiosulfate (applied from a 14% solution in water). The granules were further coated in the fluid bed with 20% salt (see table below), applied from solutions in water (25% salt, 4% titan dioxide, 1% Avedex W80, water ad 100%). Storage stability was tested as in example 1:

| Salt | % residual activity |
| --- | --- |
| 20% Na$_2$SO$_4$ (no buffer capacity) | 42 |
| 20% NaH$_2$PO$_4$ (acidic buffer component) | 74 |
| 20% Na$_2$HPO$_4$ (alkaline buffer) | 23 |

It is clear from this example that the acidic buffer component improved stability, while the alkaline buffer decreased stability compared to an "inert" (non-buffering) salt.

Percentages of salt are given as % of the weight of uncoated granulate (giving approx. 16% of the final granulate).

Example 3

Uncoated amylase was produced as in example 1 with NaH$_2$PO$_4$ as acidic buffer component and using a Lödige mixer. Part of these granules were coated with wax in a Lödige mixer as given in U.S. Pat. No. 4,106,991 example 22 using 8% PEG-4000 and 12% of a 50:50 mixture of kaolin and titan dioxide, another part was coated in a fluid bed with 20% NaH$_2$PO$_4$ as in example 2 and subsequently coated with wax as the first part using 4% PEG-4000 and 6% titan/kaolin mix.

The storage stability of the produced granulates in an ADW powder B (stored 6 weeks at 35° C. and 80% RH) was tested:

| Granulate | % NaH$_2$PO$_4$ in total | % residual activity |
| --- | --- | --- |
| NaH$_2$PO$_4$ in core | 39 | 35 |
| NaH$_2$PO$_4$ in core and in coat | 55 (40% in core and 15% in coat) | 50 |

From this example it can be seen that an increase in buffer capacity (increasing the amount of NaH$_2$PO$_4$) by using it both in the core and in the coating increases storage stability.

Example 4

Uncoated amylase was produced as in example 1 with Na$_2$SO4 as filler and using a Lödige mixer. Part of these granules (reference) were coated with wax in a Lödige mixer as given in U.S. Pat. No. 4,106,991 example 22 using 8% PEG-4000 and 12% of a 50:50 mixture of kaolin and titan dioxide, another part was coated in a UniGlaft fluid bed with 10% polyacrylic acid (applied as a 20% solution of Sokalan PA30 from BASF in adjusted to pH 5.2 with H$_2$SO$_4$) and subsequently coated with wax as the first part using 4% PEG-4000 and 6% titan/kaolin mix.

2% of the different granulates was added to ADW powder A and 2.5 grams tablets were produced on a DIAF tablet press. The stability of the tablets (stored 4 weeks at 35° C. and 55% RH) was tested:

| Granulate | % residual activity |
| --- | --- |
| Reference without buffer | 57 |
| 10% polyacrylic acid in coating | 80 |

The polyacrylic acid buffer coating increases storage stability of the tablets significantly.

What is claimed is:

1. A coated granule comprising a core and a coating, wherein the core comprises a uniform mixture of a detergent enzyme having an alkaline pH activity optimum, and 25% w/w or more of acidic buffer component, wherein said acidic buffer component is selected from the group consisting of $NaH_2PO_4$, $KH_2PO_4$ and $Na_2H$-citrate, wherein the detergent enzyme is selected from the group consisting of oxidoreductases, transferases, hydrolases, lyases, isomerases and ligases, wherein the coating comprises said acidic buffer component, and wherein the amount of acidic buffer component present in the core is more than 20% of the total amount of acidic buffer component present in the granule.

2. The granule according to claim 1, wherein the acidic buffer component has a pH of 3 to below 7.

3. The granule according to claim 1, wherein the acidic buffer component has a $pK_a$ in the range of 5 to 7.

4. The granule according to claim 1, wherein the acidic buffer component in the core and in the coating are different.

5. The granule according to claim 1, wherein the acidic buffer component in the core has a pH of 4 to below 7 and the acidic buffer component in the coating has a pH of 1 to 5.

6. The granule according to claim 1 comprising at least 55% w/w of acidic buffer component in the core.

7. The granule according to claim 1, wherein the acidic buffer component in the core and in the coating consists of $NaH_2PO_4$.

8. The granule according to claim 1, wherein the acidic buffer component in the core and in the coating consists of $KH_2PO_4$.

9. The granule according to claim 1, wherein the acidic buffer component in the core and in the coating consists of $Na_2H$-citrate.

10. The granule according to claim 1, wherein the acidic buffer component in the core and in the coating comprises $NaH_2PO_4$.

11. The granule according to claim 1, wherein the acidic buffer component in the core and in the coating comprises $KH_2PO_4$.

12. The granule according to claim 1, wherein the acidic buffer component in the core and in the coating comprises $Na_2H$-citrate.

13. The granule according to claim 1, wherein the acidic buffer component in the core and in the coating are selected from the group consisting of $NaH_2PO_4$ and $KH_2PO_4$.

14. The granule according to claim 1, wherein the acidic buffer component in the core and in the coating are selected from the group consisting of $NaH_2PO_4$ and $Na_2H$-citrate.

15. The granule according to claim 1, wherein the acidic buffer component in the core and in the coating are selected from the group consisting of $NaH_2PO_4$ and $KH_2PO_4$.

16. The granule according to claim 1, wherein the acidic buffer component in the core and in the coating are the same.

17. The granule according to claim 1, wherein the detergent enzyme is a protease.

18. The granule according to claim 1, wherein the detergent enzyme is an alpha-amylase.

19. A detergent composition comprising a granule of claim 1.

20. A process for preparing granules of claim 1 comprising:
preparing a core comprising a uniform mixture of a detergent enzyme having an alkaline pH activity optimum, and 25% w/w or more of acidic buffer component, wherein said acidic buffer component is selected from the group consisting of $NaH_2PO_4$, $KH_2PO_4$ and $Na_2H$-citrate, wherein the detergent enzyme is selected from the group consisting of oxidoreductases, transferases, hydrolases, lyases, isomerases and ligases; and
coating the core with a coating material which comprises the acidic buffer component and wherein the amount of acidic buffer component present in the core is more than 20% of the total amount of acidic buffer component present in the granule.

21. The process according to claim 20, wherein the granule is prepared in a mixer, a fluid bed, a fluidized spray dryer, a spray fluidizer, a spray dryer or an extruder.

22. A coated granule comprising a core comprising a uniform mixture of a detergent enzyme having an alkaline pH activity optimum, and 50% w/w or more of acidic buffer component, wherein said acidic buffer component is selected from the group consisting of $NaH_2PO_4$, $KH_2PO_4$ and $Na_2H$-citrate, wherein the detergent enzyme is selected from the group consisting of oxidoreductases, transferases, hydrolases, lyases, isomerases and ligases, and a coating comprising said acidic buffer component wherein the amount of acidic buffer component present in the core is more than 20% of the total amount of acidic buffer component present in the granule.

23. The granule in accordance with claim 22, wherein the acidic buffer component has a pH of 3 to below 7.

24. The granule in accordance with claim 22, wherein the acidic buffer component has a $pK_a$ in the range of 5 to 7.

* * * * *